United States Patent
Wilson et al.

(10) Patent No.: US 11,847,261 B2
(45) Date of Patent: *Dec. 19, 2023

(54) PERIODIC MOTION-BASED VISUAL STIMULUS

(71) Applicant: Microsoft Technology Licensing, LLC, Redmond, WA (US)

(72) Inventors: Andrew D. Wilson, Seattle, WA (US); Hakim Si Mohammed, Rennes (FR); Christian Holz, Seattle, WA (US); Adrian Kuo Ching Lee, Newcastle, WA (US); Ivan Jelev Tashev, Kirkland, WA (US); Hannes Gamper, Seattle, WA (US); Edward Bryan Cutrell, Seattle, WA (US); David Emerson Johnston, Bellevue, WA (US); Dimitra Emmanouilidou, Kirkland, WA (US); Mihai R. Jalobeanu, Bellevue, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/815,532

(22) Filed: Jul. 27, 2022

(65) Prior Publication Data
US 2022/0365599 A1 Nov. 17, 2022

Related U.S. Application Data

(63) Continuation of application No. 16/780,173, filed on Feb. 3, 2020, now Pat. No. 11,409,361.

(51) Int. Cl.
*G06F 3/01* (2006.01)
*G06F 1/16* (2006.01)
(Continued)

(52) U.S. Cl.
CPC .............. *G06F 3/015* (2013.01); *A61B 5/378* (2021.01); *G01R 19/0084* (2013.01); *G02B 27/0176* (2013.01); *G06F 1/163* (2013.01)

(58) Field of Classification Search
CPC .......... G06F 3/015; G06F 1/163; A61B 5/378
See application file for complete search history.

(56) References Cited

U.S. PATENT DOCUMENTS

| 11,409,361 | B2* | 8/2022 | Wilson | G06F 3/015 |
| 2013/0130799 | A1* | 5/2013 | Van Hulle | A61B 5/378 463/36 |
| 2018/0188807 | A1* | 7/2018 | Cimenser | A61B 5/18 |

* cited by examiner

*Primary Examiner* — Mark Edwards
*Assistant Examiner* — Chayce R Bibbee
(74) *Attorney, Agent, or Firm* — Alleman Hall Creasman & Tuttle LLP

(57) ABSTRACT

A computer device is provided that includes a display device, and a sensor system configured to be mounted adjacent to a user's head and to measure an electrical potential near one or more electrodes of the sensor system. The computer device further includes a processor configured to present a periodic motion-based visual stimulus having a changing motion that is frequency-modulated for a target frequency or code-modulated for a target code, detect changes in the electrical potential via the one or more electrodes, identify a corresponding visual evoked potential feature in the detected changes in electrical potential that corresponds to the periodic motion-based visual stimulus, and recognize a user input to the computing device based on identifying the corresponding visual evoked potential feature.

15 Claims, 12 Drawing Sheets

(51) Int. Cl.
*A61B 5/378* (2021.01)
*G01R 19/00* (2006.01)
*G02B 27/01* (2006.01)

300

PRESENTING A PERIODIC MOTION-BASED VISUAL STIMULUS HAVING A CHANGING MOTION THAT IS FREQUENCY-MODULATED FOR A TARGET FREQUENCY OR CODE-MODULATED FOR A TARGET CODE VIA A DISPLAY DEVICE OF THE COMPUTER DEVICE 302

DETECTING CHANGES IN THE ELECTRICAL POTENTIAL VIA THE ONE OR MORE ELECTRODES 304

IDENTIFYING A CORRESPONDING VISUAL EVOKED POTENTIAL FEATURE IN THE DETECTED CHANGES IN ELECTRICAL POTENTIAL THAT CORRESPONDS TO THE PERIODIC MOTION-BASED VISUAL STIMULUS 306

RECOGNIZING A USER INPUT TO THE COMPUTING DEVICE BASED ON IDENTIFYING THE CORRESPONDING VISUAL EVOKED POTENTIAL FEATURE 308

FIG. 3

PERIODIC MOTION-BASED VISUAL STIMULUS

CROSS REFERENCE TO RELATED APPLICATIONS

This application is a continuation of U.S. patent application Ser. No. 16/780,173, filed Feb. 3, 2020, the entirety of which is hereby incorporated herein by reference for all purposes.

BACKGROUND

Brain-Computer Interfaces may be used to transform brain activity into computer input. One of the fastest BCI paradigms to detect and extract brain signals is Steady-State Visual Evoked Potentials (SSVEP). These types of BCI rely on the neurophysiological property that when an individual focuses on a periodic visual stimulus, the power of the brain activity at the same frequency increases as the strength of the stimulus increases.

SUMMARY

A computer device is provided. The computer device may comprise a display device, and a sensor system configured to be mounted adjacent to a user's head and to measure an electrical potential near one or more electrodes of the sensor system. The computer device may further include a processor configured to present a periodic motion-based visual stimulus having a changing motion that is frequency-modulated for a target frequency or code-modulated for a target code, detect changes in the electrical potential via the one or more electrodes, identify a corresponding visual evoked potential feature in the detected changes in electrical potential that corresponds to the periodic motion-based visual stimulus, and recognize a user input to the computing device based on identifying the corresponding visual evoked potential feature.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIG. 3 shows a flowchart for an example method of implementing periodic motion-based visual stimulus for VEP interfaces implemented by the computer device of FIG. 1.

DETAILED DESCRIPTION

Figure 1:
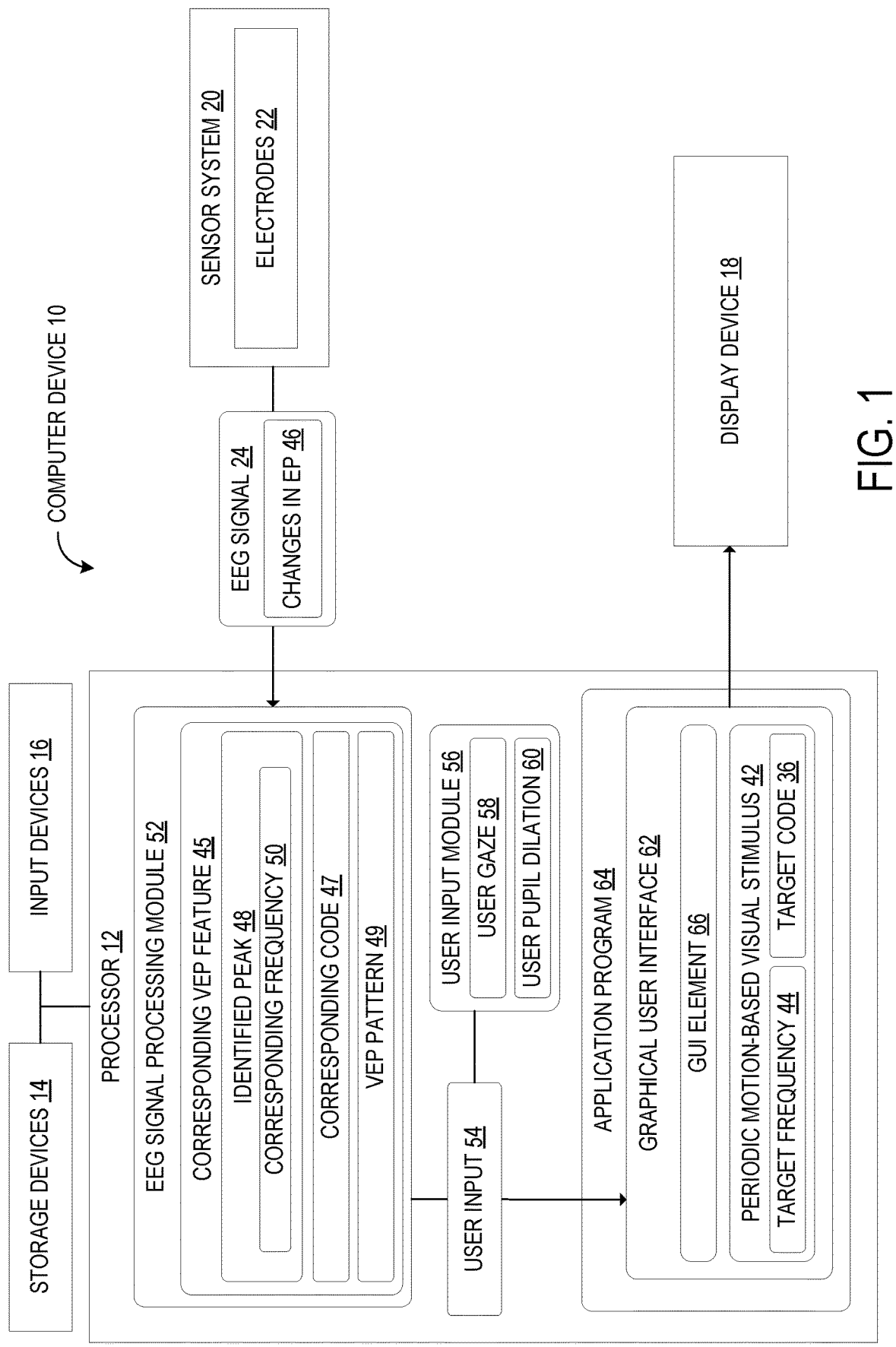
FIG. 1 shows an example computer device that implements a periodic motion-based visual stimulus for visual evoked potential (VEP) interfaces according to one embodiment of the present disclosure.

Typical VEP interfaces, such as Steady State Visual Evoked Potential interfaces, are often fatigue-inducing and rely on overlaying blinking objects on the interface that may cause visual fatigue and annoyance for viewers of the blinking stimuli. To address this issue, FIG. 1 illustrates an example computer device 10 that implements a periodic motion-based visual stimulus for VEP interfaces that reduces visual fatigue and increases the user-friendliness of VEP interfaces while preserving classification accuracy. The computer device 10 includes a processor 12, storage devices 14, an input device 16, a display device 18, a sensor system 20, and other suitable computer components configured to implement the techniques and processes described herein. In one example, the computer device 10 may take the form of a desktop computer device, a laptop computer device, or another suitable type of computer device. In this example, the display device 18 may take the form of a display monitor, a large format display, a projector, a display integrated in a mobile device, etc. The storage devices 14 may include volatile and non-volatile storage devices configured to store instructions to be executed by the processor 12. The input devices 16 may include one or more input devices, such as, for example, a keyboard, a mouse, one or more camera devices, a microphone, etc.

The sensor system 20 of the computer device 10 is configured to be mounted adjacent to the user's head and to measure an electrical potential near one or more electrodes 22 of the sensor system 20. For example, the sensor system 20 may take the form of an electroencephalography (EEG) device configured to capture an EEG signal 24 that measures voltage fluctuations near the electrodes 22 that may result from neuronal activity of the user's brain. The sensor system 20 may be configured to measure event-related potentials for potential fluctuations time locked to presentation of a periodic motion-based visual stimulus, as will be discussed in more detail below.

Figure 2B:
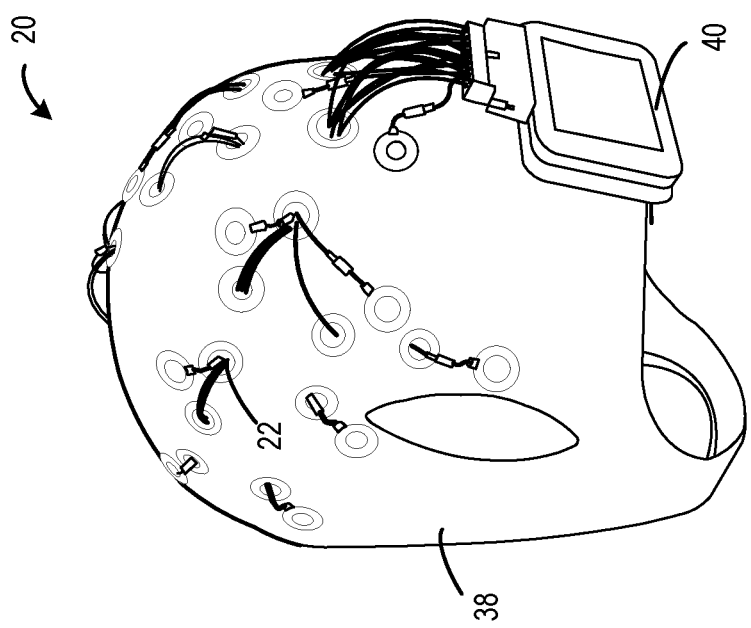
FIG. 2B shows an example sensor system integrated into a wearable item for the computer device of FIG. 1.
Figure 2A:
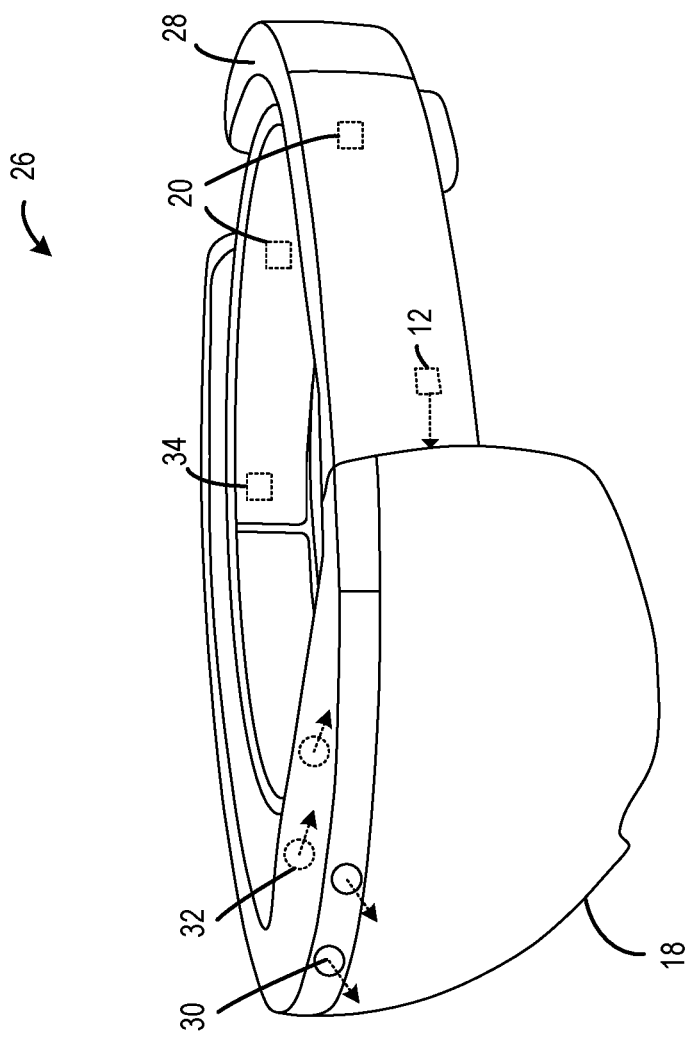
FIG. 2A shows an example head mounted display device and sensor system for the computer device of FIG. 1.

In another example, the computer device 10 may take the form of a head mounted display (HMD) device. FIG. 2A shows an example of the computer device 10 in the form of an HMD device 26. The HMD device 26 may be worn by a user according to an example of the present disclosure. In other examples, an HMD device may take other suitable forms in which an at least partially see-through display is supported in front of a viewer's eye or eyes in an augmented reality HMD device configuration.

In the example of FIG. 2A, the HMD device 26 includes a frame 28 that wraps around the head of the user to position the display device 18, which takes the form of a near-eye display in this example, close to the user's eyes. The frame supports additional components of the HMD device 26, such as, for example, the processor 12, input devices 16 that may include one or more outward facing cameras 30 and/or one or more inward facing cameras 32. The processor 12 includes logic and associated computer memory configured to provide image signals to the display device 18, to receive sensory signals from outward facing cameras 30, inward facing cameras 32, other types of input devices 16, and to enact various control processes described herein.

Any suitable display technology and configuration may be used to display images via the display device 18. For example, in a non-augmented reality configuration, the display device 18 may be a non-see-through Light-Emitting Diode (LED) display, a Liquid Crystal Display (LCD), or any other suitable type of non-see-through display. In an augmented reality configuration, the display device 18 may be configured to enable a wearer of the HMD device 26 to view a physical, real-world object in the physical environment through one or more partially transparent pixels displaying virtual object representations. For example, the display device 18 may include image-producing elements such as, for example, a see-through Organic Light-Emitting Diode (OLED) display.

As another example, the HMD device 26 may include a light modulator on an edge of the display device 18. In this example, the display device 18 may serve as a light guide for delivering light from the light modulator to the eyes of a wearer. In other examples, the display device 18 may utilize a liquid crystal on silicon (LCOS) display.

The input devices 14 may include various sensors and related systems to provide information to the processor 12. Such sensors may include an inertial measurement unit (IMU) 34. The one or more inward facing camera devices 32 may be configured to acquire image data in the form of gaze tracking data and/or pupil dilation data from a wearer's eyes.

The one or more outward facing camera devices 30 may be configured to capture and/or measure physical environment attributes of the physical environment in which the HMD device 26 is located. In one example, the one or more outward facing camera devices 30 may include a visible-light camera or RBG camera configured to collect a visible-light image of a physical space. Further, the one or more outward facing camera devices 30 may include a depth camera configured to collect a depth image of a physical space. More particularly, in one example the depth camera is an infrared time-of-flight depth camera. In another example, the depth camera is an infrared structured light depth camera.

Data from the outward facing camera devices 30 may be used by the processor 12 to generate and/or update a three-dimensional (3D) model of the physical environment. Data from the outward facing camera devices 30 may be used by the processor 12 to identify surfaces of the physical environment and/or measure one or more surface parameters of the physical environment. In augmented reality configurations of HMD device 26, the position and/or orientation of the HMD device 26 relative to the physical environment may be assessed so that augmented-reality images may be accurately displayed in desired real-world locations with desired orientations.

In both augmented reality and non-augmented reality configurations of HMD device 26, the IMU 34 of HMD device 26 may be configured to provide position and/or orientation data of the HMD device 26 to the processor 12. In one implementation, the IMU 34 may be configured as a three-axis or three-degree of freedom (3DOF) position sensor system. This example position sensor system may, for example, include three gyroscopes to indicate or measure a change in orientation of the HMD device 26 within 3D space about three orthogonal axes (e.g., roll, pitch, and yaw). In another example, the IMU 34 may be configured as a six-axis or six-degree of freedom (6DOF) position sensor system. Such a configuration may include three accelerometers and three gyroscopes to indicate or measure a change in location of the HMD device 26 along three orthogonal spatial axes (e.g., x, y, and z) and a change in device orientation about three orthogonal rotation axes (e.g., yaw, pitch, and roll). The orientation derived from the sensor signals of the IMU may be used to display, via the display device 18, one or more holographic images with a realistic and stable position and orientation. In some implementations, position and orientation data from the outward facing camera devices 30 and the IMU 34 may be used in conjunction to determine a position and orientation (or 6DOF pose) of the HMD device 26.

In some examples, a 6DOF position sensor system may be used to display holographic representations in a world-locked manner. A world-locked holographic representation appears to be fixed relative to one or more real world objects viewable through the HMD device 26, thereby enabling a wearer of the HMD device 26 to move around a real world physical environment while perceiving a world-locked hologram as remaining stationary in a fixed location and orientation relative to the one or more real world objects in the physical environment.

In one example, the sensor system 20 may be integrated with the HMD device 26. For example, a portion of the frame 28 located near a back of a wearer's head may include one or more electrodes 22 of the sensor system 20. In this manner, the electrodes of the sensor system 20 may be mounted adjacent a user's head when the user is wearing the HMD device 26. In another example, the sensor system 20 may be mounted to the frame 28 and extend outward from the frame 28 such that one or more electrodes 22 of the sensor system 24 are positioned adjacent to the user's head.

However, it should be appreciated that other mounting configurations may be used to position the sensor system 20 adjacent to the user's head. FIG. 2B illustrates an example sensor system 20 that is integrated into a wearable item 38. When worn, one or more electrodes 22 may be positioned in contact with or near the wearer's scalp. In the example illustrated in FIG. 2B, a plurality of electrodes 22 are mounted to encompass a user's head. However, in another example, the plurality of electrodes 22 may all be mounted adjacent to a back of the user's head near a visual cortex of the user's brain. However, it should be appreciated that other mounting schemes may be used to position one or more electrodes 22 adjacent to the user's head.

The one or more electrodes 22 may be configured to measure an electrical potential resulting from neuronal activity of the user's brain near the electrodes 22. In one example, EEG signals 24 from the one or more electrodes 22 may be gathered by a signal processing device 40 of the sensor system 20. The signal processing device 40 may be configured to communicate the EEG signals 24 to the processor 12 of the computer device 10. The signal processing device 40 may send the data for the EEG signals 24 to the processor 12 using wireless or wired communication techniques. In one example, the signal processing device 40 may be configured to perform signal processing techniques on the EEG signals 24 described herein. In another example, the signal processing device 40 may be configured to send data for the EEG signals 24 without performing those signal processing techniques.

The wearable item 38 integrated with the sensor system 20 may be worn in addition to the HMD device 26 by a user. In non-HMD device examples of the computer device 10, the wearable item 38 may be worn individually by the user. In either example, the EEG signals 24 from the sensor system 20 worn by the user may be communicated to the processor 12 of the computer device 10.

Figure 5:
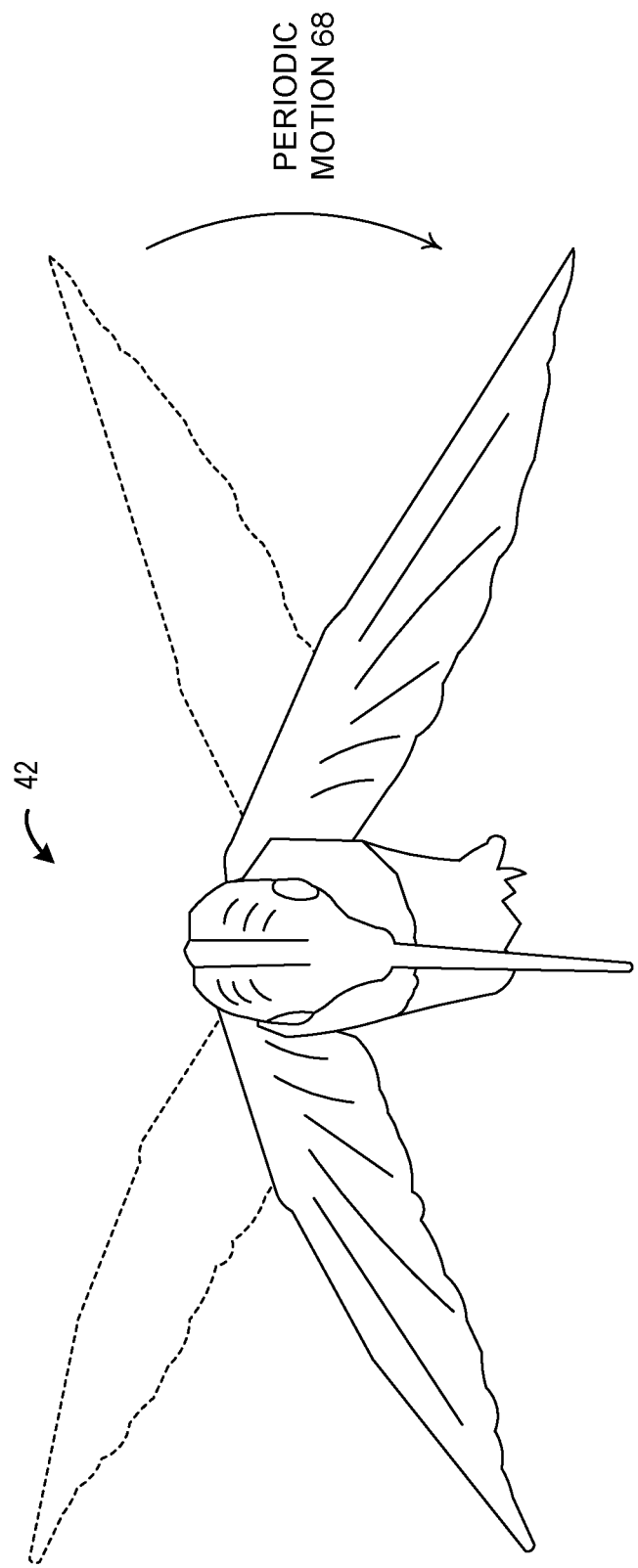
FIG. 5 shows an example periodic motion-based visual stimulus displayed by the computer device of FIG. 1.
Figure 6:
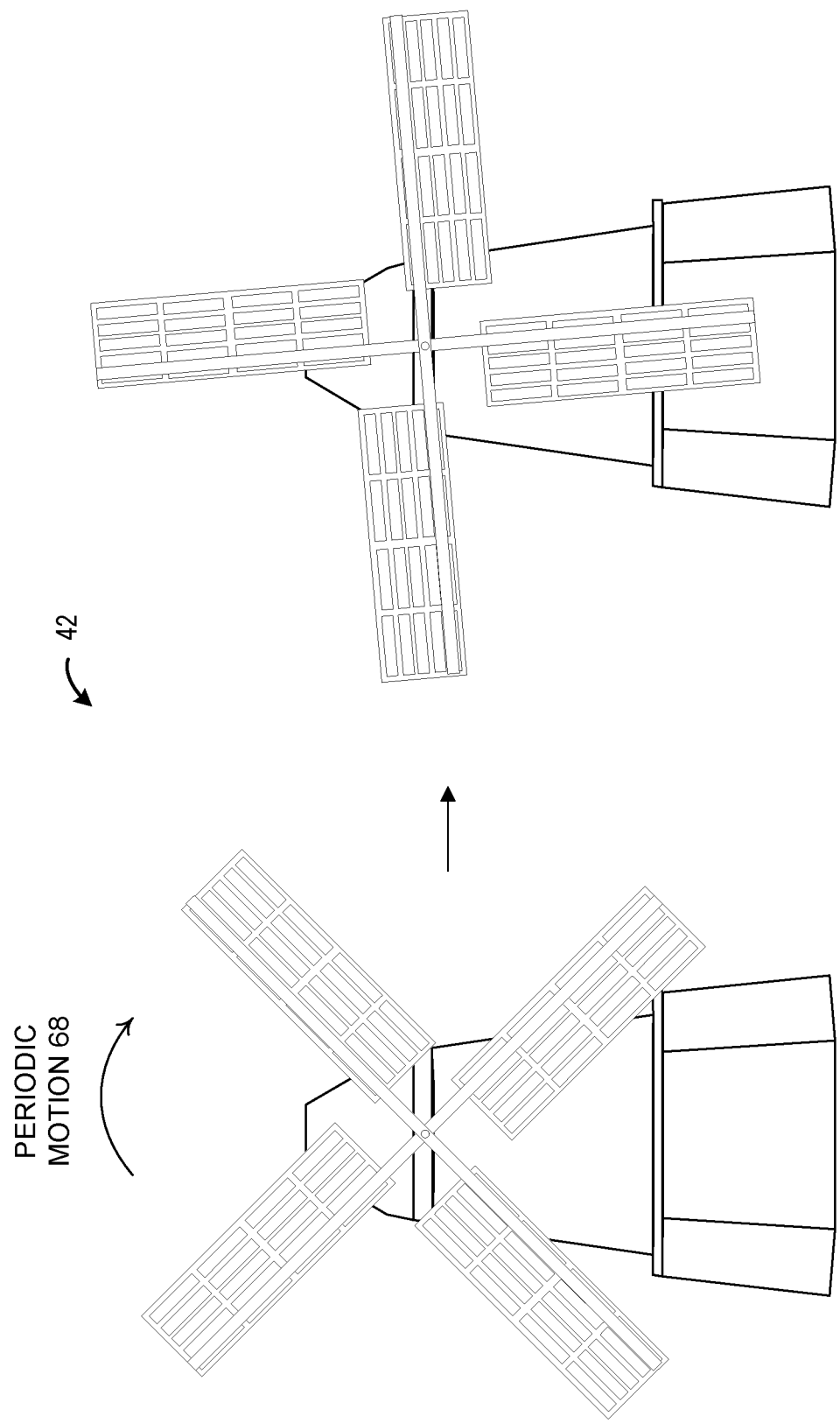
FIG. 6 shows another example periodic motion-based visual stimulus displayed by the computer device of FIG. 1.
Figure 7:
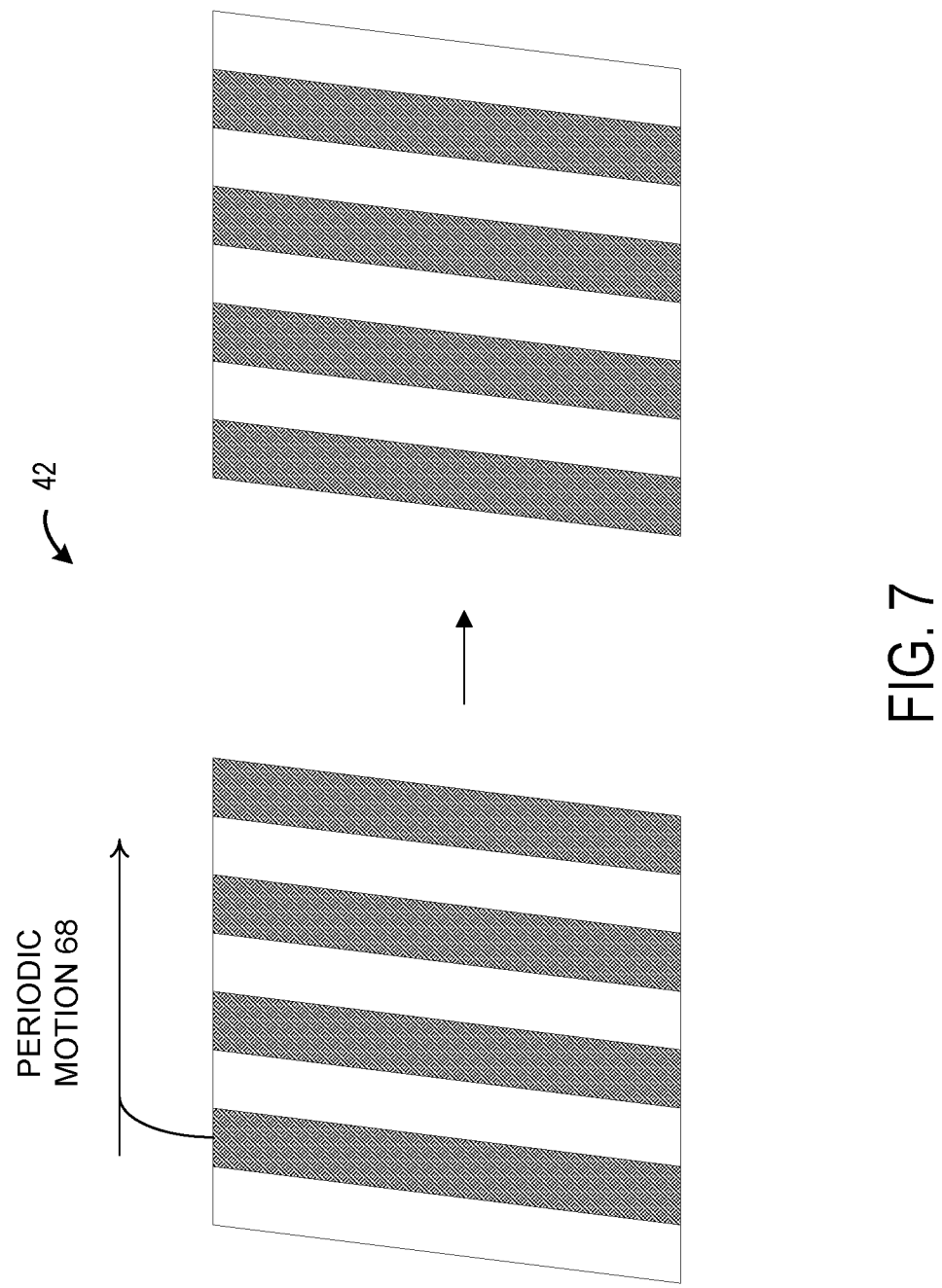
FIG. 7 shows another example periodic motion-based visual stimulus displayed by the computer device of FIG. 1.

Turning briefly to FIG. 3, the processor 12 of the computer device 10 may be configured to implement a method 300 for implementing a periodic motion-based visual stimulus for VEP interfaces that reduces visual fatigue and increases the user-friendliness of VEP interfaces while preserving classification accuracy. At step 302, the method 300 may include presenting a periodic motion-based visual stimulus 42 having a changing motion that is frequency-modulated for a target frequency 44 or code-modulated for a target code 36 via the display device 18. Several example periodic motion-based visual stimuli 42 are illustrated in FIGS. 5-7 and described in more detail below.

In one example, the periodic motion-based visual stimulus 42 may be configured to be frequency-modulated such that a changing motion of the stimulus moves at target frequency 44. The target frequency 44 may, for example, include a fundamental frequency of the change in periodic motion of the visual stimulus 42. The target frequency 44 may, for example, be in the range of 6 Hz to 30 Hz, such as 8 Hz, 10 Hz, 12 Hz, etc. However, it should be appreciated that the target frequency 44 may be set to other values and ranges of frequencies that are suitable for producing an SSVEP. As shown in FIG. 1, the periodic motion-based visual stimulus 42 is sent to the display device 18 for presentation to the user.

In another example, the periodic motion-based visual stimulus 42 may be configured to be code-modulated such that the changing motion of the stimulus moves according to a target code 36. As a specific example, the processor 12 may be configured to use a pseudorandom code, such as an m-sequence, with a low auto-correlation which may be shifted for different target codes 36. However, it should be appreciated that other types of techniques may be used to code-modulate the periodic motion-based visual stimulus 42.

As described herein, the periodic motion-based visual stimulus 42 that may be frequency-modulated or code-modulated may cause a predictable VEP in a viewer's brain that may be detected via the one or more electrodes of the sensor system 20. However, it should be appreciated that the periodic motion-based visual stimulus 42 is not limited to only the example frequency-modulation and code-modulation techniques described herein, and may implement other types of VEP techniques.

Returning to FIG. 3, at step 304, the method 300 may include detecting changes in the electrical potential 46 via the one or more electrodes 22. While the periodic motion-based visual stimulus 42 is being presented via the display device 18, the sensor system 20 may be configured to detect changes in electrical potential 46 via the electrodes 22. As discussed above, these detected changes in electrical potential 46 reflect neuronal activity of the user's brain detected through the skull/scalp of the user via the adjacently mounted sensor system 20. For example, the user may be wearing the wearable item 38 that integrates the sensor system 20 illustrated in FIG. 2B. The captured data for the changes in electrical potential 46 may be sent to the processor 12 of the computer device 10 as the EEG signal 24 shown in FIG. 1.

Continuing with FIG. 3, at step 306, the method 300 may include identifying a corresponding visual evoked potential feature 45 in the detected changes in electrical potential 46 that corresponds to the periodic motion-based visual stimulus 42. In one example, the periodic motion-based visual stimulus 42 may be frequency-modulated to change at a target frequency 44. To identify the corresponding visual evoked potential feature 45, the EEG signal processing module 52 may be configured to identify a peak 48 in a frequency domain of the detected changes in electrical potential 46 at a corresponding frequency 50 that corresponds to the target frequency 44 of the periodic motion-based visual stimulus 42. As illustrated in FIG. 1, the EEG signal 24 received from the sensor system 20 may be processed by an EEG signal processing module 52 executed by the processor 12.

Typically, when the human eye is excited by a visual stimulus, such as, for example, the periodic motion-based visual stimulus 42, the brain may generate electrical activity at a same frequency or multiple of the frequency of the visual stimulus. That brain activity may be detected by the sensor system 20 and reflected in the EEG signal 24 captured by the sensor system 20. In this manner, when the user views the presented periodic motion-based visual stimulus 42, a corresponding VEP may be reflected in the electrical activity of the user's brain that may be observed in the oscillatory components (e.g. frequency domain) of the EEG signal 24 captured by the sensor system. In the frequency domain of the EEG signal 24, the target frequency 44 of the periodic motion-based visual stimulus 42 and higher harmonics may be recognized by the EEG signal processing module 52.

In one example, the EEG signal processing module 52 may be configured to perform several processing steps on the data of the EEG signal 24. As a specific example, the EEG signal processing module 52 may perform a preprocessing step in order to remove or dampen the effects of noise and artifacts in the EEG signal. The EEG signal processing module 52 may be further configured to perform feature recognition to identify one or more peaks in the frequency domain of the EEG signal 24 that are likely to be associated with an SSVEP rather than a noise or artifact in the EEG signal 24. The EEG signal processing module 52 may then be configured to determine whether a frequency associated with identified peak in the EEG signal 24 corresponds to a target frequency 44 of a periodic motion-based visual stimulus 42 being presented via the display device 18. For example, the EEG signal processing module 52 may be configured to identify peaks 48 at corresponding frequencies 50 that correspond to the fundamental frequency and upper harmonic frequencies of the periodic motion-based visual stimulus 42.

In one example, the periodic motion-based visual stimulus 42 may provide a visual stimulus that only has a fundamental frequency and does not have any upper harmonic frequencies. Nonetheless, due to non-linearities of the brain including the eye structure and visual cortex, the electrical activity of the user's brain may include SSVEPs at both the fundamental frequency of the visual stimulus as well as upper harmonics that are multiples of the fundamental frequency. The EEG signal processing module 52 may be configured to identify the peaks associated with each of those frequencies, and correlate those peaks to the target frequency 44 of the periodic motion-based visual stimulus 42.

In another example, the periodic motion-based visual stimulus 42 may include more complex motions that have both a fundamental frequency and upper harmonic frequencies. In a similar manner, the EEG signal processing module 42 may be configured to identify the peaks associated with each of those frequencies, and correlate those peaks to the target frequency 44 of the periodic motion-based visual stimulus 42. These more complex motions that include both a fundamental frequency and upper harmonics may potentially provide an improved classification accuracy of the EEG signal processing module 52 for correlating peaks 48 in the EEG signal 24 to specific periodic motion-based visual stimuli 42.

As discussed above, the periodic motion-based visual stimulus 42 may alternatively be code-modulated using a pseudorandom code with a low auto-correlation which is shifted for the different target codes 36. To identify the corresponding VEP feature 45, the EEG signal processing module 52 may be configured to identify a corresponding code 47 in the detected changes in electrical potential 46 that corresponds to the target code 36 of the periodic motion-based visual stimulus 42.

As another example, the EEG signal processing module 52 may be configured to identify a VEP pattern 49 as the corresponding VEP feature 45. For example, the EEG signal processing module 45 may be calibrated for a user during a calibration phase where periodic motion-based visual stimuli 42 at different target frequencies and/or codes are presented to a user that is instructed to view the stimuli. Then, a resulting EEG signal 24 for the user may be stored as VEP patterns 49 and associated with the presented periodic motion-based visual stimulus 42. Noise suppression and feature extraction techniques may be used to process these stored VEP patterns 49. Next, during run-time, a current EEG signal 24 may be detected and compared to the stored VEP patterns 49, which may include a spectrum of different VEP features, to identify the corresponding VEP feature 45 that corresponds to the periodic motion-based visual stimulus 42 being displayed via the display device 18. It should be appreciated the EEG signal processing module 52 may use other types of VEP feature identification techniques not specifically described herein.

Returning to FIG. 3, at step 308, the method 300 may include recognizing a user input 54 to the computing device 10 based on identifying the corresponding visual evoked potential feature 45. In the example of FIG. 1, the recognition of the user input 54 may be included in a gaze detection process executed by the processor 12. For example, the processor 12 may be further configured to execute a user input module 56 that determines where a user is looking and recognizes user inputs based on a gaze direction of the user. For example, the user input module 56 may determine whether the user is gazing at a particular virtual object being presented by the display device 18, and may recognize the user's gaze as a user input, such as a selection input, to that particular virtual object. In an augmented reality configuration where a real-world object/environment may be viewable behind the displayed virtual objects, it may be difficult for typical HMD devices to determine whether the user is focusing their attention on the virtual object or the real-world environment behind the virtual object. As will be discussed in more detail below, including a periodic motion-based visual stimulus 42 with these virtual objects may allow the HMD device to determine whether or not the user is attending to that virtual object. In this manner, the VEP techniques described herein may be combined with typical user gaze 58 and/or user pupil dilation 60 techniques to provide an improved accuracy in identifying what the user is intending to view.

In one example, the recognized user input 54 may be used by the computer device 10 as input to a graphical user interface 62. In the example illustrated in FIG. 1, the processor 12 may be further configured to execute an application program 64 that includes the GUI 62. The GUI 62 may include various GUI elements 66 that include visuals presented via the display device 18. One or more of those GUI elements 66 may be associated with respective periodic motion-based visual stimuli 42 having differentiated target frequencies 44 or target codes 36 based on whether the periodic motion-based visual stimuli 42 are frequency-modulated or code-modulated. Based on identifying the corresponding VEP feature 45 in the EEG signal 24, the processor 12 may be configured to recognize a user input directed to the associated GUI element 66. For example, the user input may be recognized as a user selection of that GUI element 66. The user input 54 may be sent to the application program 64, which may then perform a GUI actions based on that user input 54. It should be appreciated that any suitable user input related actions may be performed by the application program 64 in response to the user input 54.

Figure 4:
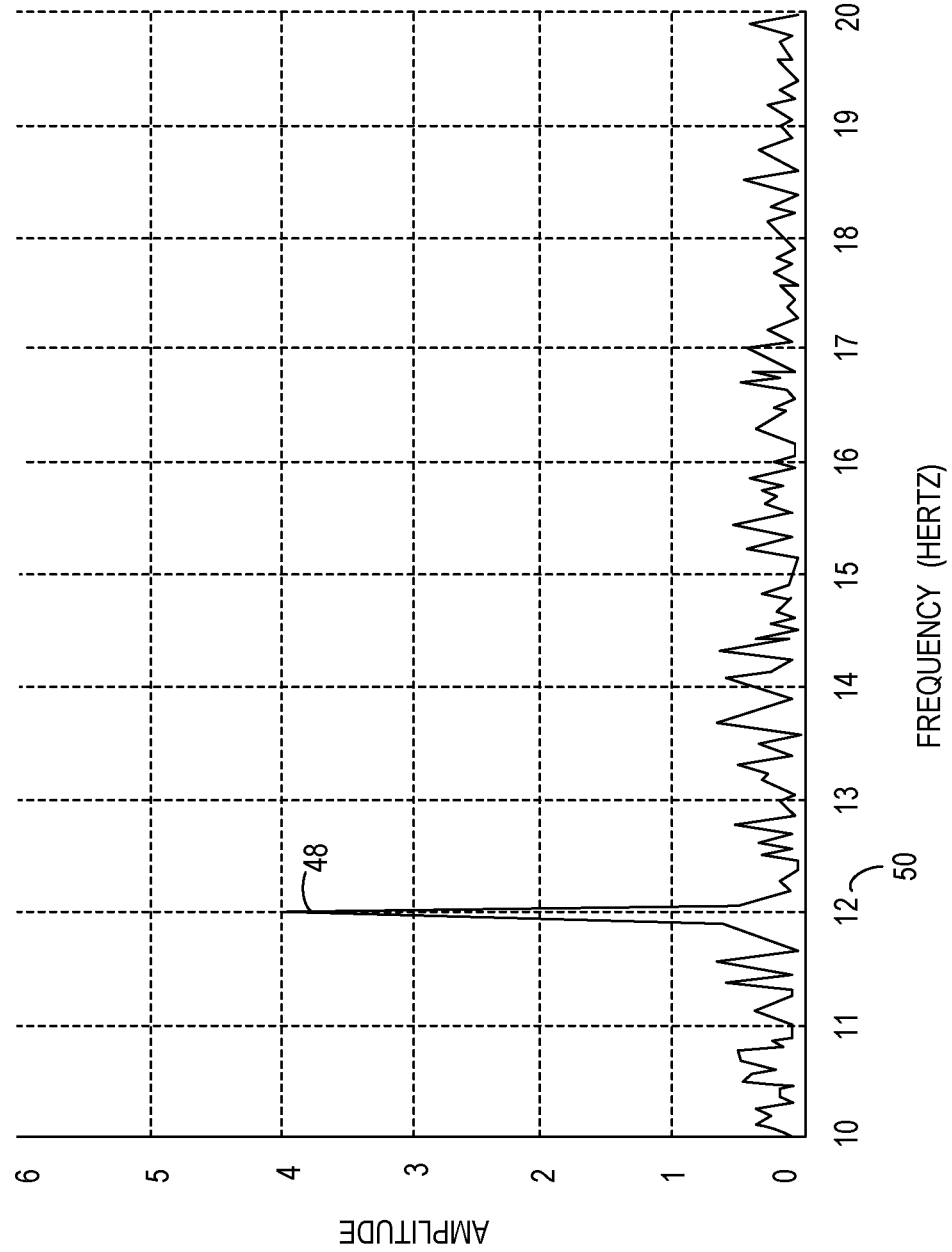
FIG. 4 shows a graph of a frequency domain of electrical activity of a user's brain captured by a sensor system of the computer device of FIG. 1.

FIG. 4 shows graph of a frequency domain of an example EEG signal 24 for a user viewing a periodic motion-based visual stimulus 42 having a target frequency 44 of 12 Hz. While the user attends to the periodic motion-based visual stimulus 42 being presented via the display device 18, the sensor system 20 captures an EEG signal 24 that includes data for the changes in electrical potential 46 detected by the electrodes 22 of the sensor system 20. The EEG signal processing module 52 processes the EEG signal 24, and identifies one or more peaks in the frequency domain of the EEG signal 24, such as, for example, the peak 48 illustrated in FIG. 4. The EEG signal processing module 52 may then compare a frequency of the signal at the peak 48, which is 12 Hz in the illustrated example, to the target frequencies 44 of each displayed periodic motion-based visual stimulus 42. In this example, the EEG signal processing module 52 may determine that the frequency of the peak 48 corresponds to the target frequency 44 of the currently displayed periodic motion-based visual stimulus 42. Based on this determination, the processor 12 of the computer device 10 may then recognize a user input 54, and may perform a process based on that user input 54 such as, for example, causing a selection of a GUI element 66 associated with that periodic motion-based visual stimulus.

A similar process may be performed when identifying corresponding codes 47 in the EEG signal 24. For example, the EEG signal processing module 52 may process the EEG signal 24 to identify peaks at different frequencies over a time-domain of the EEG signal 24, and may identify the corresponding code 47 based on the changing VEPs. However, it should be appreciated that other techniques and processes may be utilized by the EEG signal processing module 52 to identify the corresponding code 47.

FIG. 5 illustrates an example type of periodic motion-based visual stimulus 42. The example periodic motion-based visual stimulus 42 is an animation of a winged creature, which in this case is a hummingbird, flapping its wings. For a frequency-modulated stimulus, the animation of the winged creature may flap its wings at a target frequency 44. For a code-modulated stimulus, the animation of the winged creature may flap its wings according to, for example, a pseudorandom code with a low auto-correlation which is shifted for different target codes 36. It will be appreciated that winged creatures other than hummingbirds may alternatively be depicted, and in addition motions of other portions of creatures that are periodic in nature may be used, as winged creatures are simply one example implementation. In this example, the motion of the wings of the hummingbird includes a periodic motion 68 in the form of a rotational motion that moves in an arc around a fixed point where the wings attach to the hummingbird. The periodic motion 68 of the wings may be frequency-modulated to be set to a target frequency, such as, for example, 12 Hz. In this example, the target frequency may be defined as the number of complete wing flap motions per second. Thus, if the wings of the animated hummingbird flap 12 times per second, then the periodic motion-based visual stimulus 42 of FIG. 5 may have a target frequency 42 having a fundamental frequency of 12 Hz. Alternatively, the periodic motion 68 of the wings may be code-modulated for a target code 36.

However, it should be appreciated that the periodic motion 68 of a bird's wing flap is a complex motion and may include other upper harmonic frequencies. Thus, when viewed by a user, the periodic motion-based visual stimulus 42 of the hummingbird's wings may be reflected in the visual cortex of the user as electrical activity having multiple peaks at different frequencies including the fundamental frequency and upper harmonic frequencies. Each of these peaks and the corresponding frequencies may be used by the EEG signal processing module 52 to classify the EEG signal as including electrical activity that reflects the user viewing the periodic motion-based visual stimulus 42. In this manner, the processor 12 may to recognize the user input 54 based on identifying peaks 48 at corresponding frequencies 50 that correspond to the fundamental frequency and upper harmonic frequencies of the periodic motion-based visual stimulus 42.

In one example, the periodic motion-based visual stimulus 42 may take the form of a rapid serial visual presentation of images. For example, the periodic motion-based visual stimulus 42 may include a plurality of two or three-dimensional images that are sequentially displayed to achieve a target frequency 44 or target code 36. In the example illustrated in FIG. 5, a plurality of images for different positions of the hummingbird's wings may be sequentially presented to the user via the display device 18 in a rapid serial visual presentation. Presentation of the images may be slowed or sped up to achieve a suitable target frequency 44 or target code 36 for the periodic motion 68 of the hummingbird's wings.

In another example, the periodic motion-based visual stimulus 42 may take the form of an animated three-dimensional virtual object presented by the display device 18. In HMD device 26 forms of the computer device 10, the animated three-dimensional virtual object may be presented via the near-eye display device of the HMD device 26. In an augmented reality HMD device 26 example, the animated three-dimensional virtual object may take the form of a virtual hologram that is presented via an at least partially see-through display device of the HMD device 26.

As discussed above, the HMD device 26 may use various sensor devices such as the IMU 34 and outward facing camera devices 30 to orient the HMD device 26 in the physical space of the real-world and display the virtual hologram at a position in the real-world environment via the at least particularly see-through display. In one example, the virtual hologram may be displayed at a world-locked position such that the hologram appears to be located at the same position as the user moves around the real-world. In another example, the hologram may be displayed at a position locked to a view of the HMD device 26, such as, for example, in a heads-up display GUI configuration. In these examples, animation of the virtual object/hologram may be slowed down or sped up to achieve the target frequency 44 or target code 36 for the periodic motion-based visual stimulus 42.

FIG. 6 shows an example periodic motion-based visual stimulus 42 in the form of a windmill animation. As illustrated, the periodic motion-based visual stimulus 42 includes a periodic motion 68 in the form of a rotational motion of the windmill arms that rotate around a fixed point. The target frequency 44 of the windmill periodic motion-based visual stimulus may be based on the number of rotations of the windmill arms per second. Thus, the target frequency 44 may be increased or decreased by changing a speed of rotation of the windmill arms. Similarly, the windmill periodic motion-based visual stimulus may be code-modulated such that the speed of rotation of the windmill arms changes according to the target code 36. Alternatively, other structures or machines that feature components that exhibit periodic motion-based visual effects may be used.

FIG. 7 shows an example periodic motion-based visual stimulus 42 in the form of a grating pattern that includes moving bars. The movements of the changing grating pattern may form the periodic motion 68. The target frequency 44 of the changing grating pattern periodic motion-based visual stimulus may be based on the number of bars of the grating pattern that pass a particular location per second. Thus, the target frequency 44 may be increased or decreased by changing a speed of motion of the bars of the changing grating pattern. Although the example illustrated in FIG. 7 shows a horizontally changing pattern, it should be appreciated that the periodic motion-based visual stimulus 42 may take the form of a vertically changing grating pattern, a rotationally changing grating pattern etc.

Additionally, it should be appreciated that the periodic motion-based visual stimulus 42 is not limited to the examples illustrated in FIGS. 5-7. As another example, the periodic motion-based visual stimulus 42 may include a periodic motion in the form of an oscillation motion. For example, a pendulum that swings at a target frequency, a person that is jump roping at a target frequency, a string vibrating at a target frequency, etc. Further, it should be appreciated that other types of periodic motion 68 not specifically described herein may be utilized by the periodic motion-based visual stimulus 42.

Figure 8:
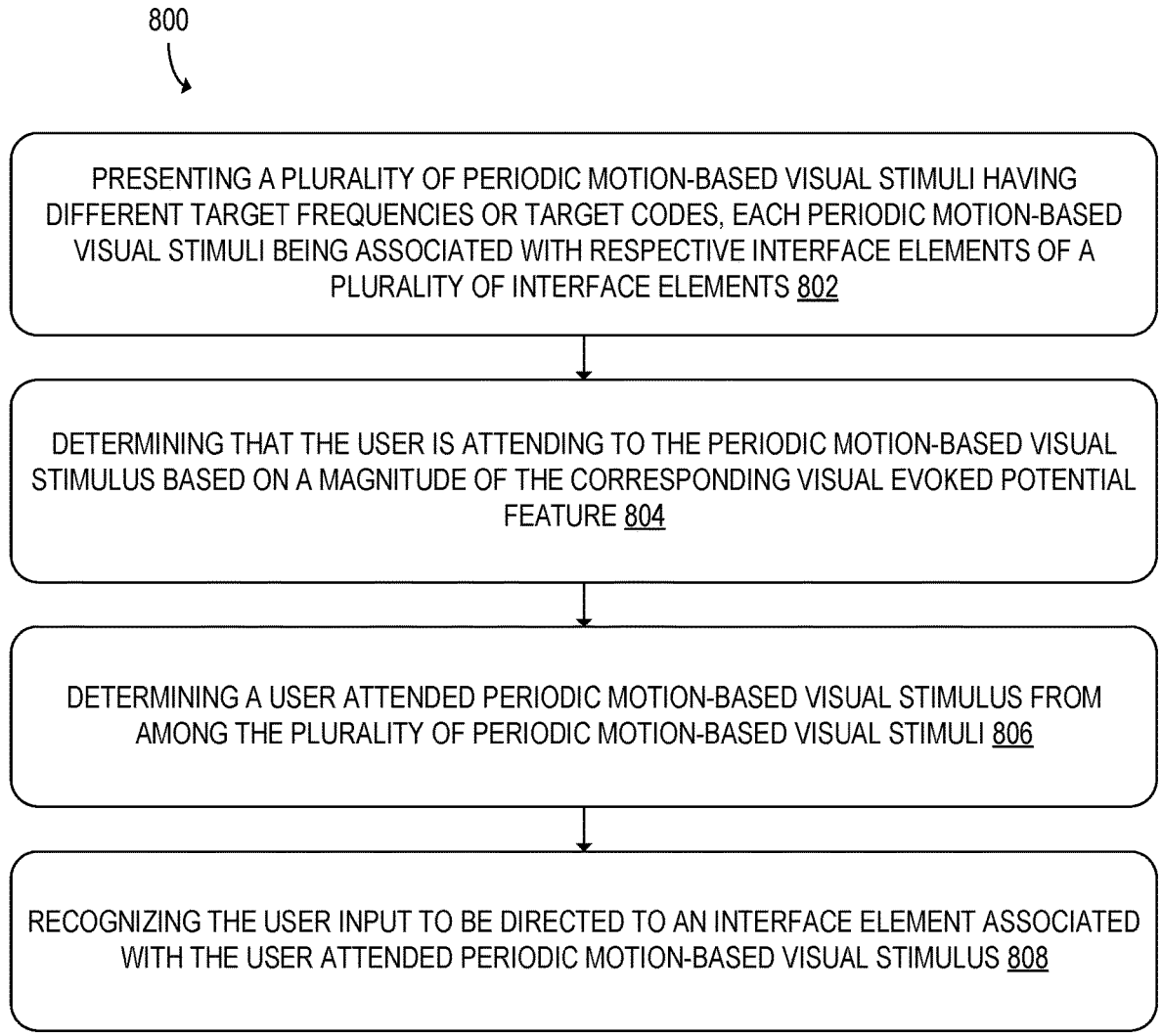
FIG. 8 shows a flowchart for an example method of determining a user attended periodic motion-based visual stimulus implanted by the computer device of FIG. 1.

FIG. 8 shows a flowchart for a method 800 for determine which periodic motion-based stimulus from among a plurality of stimuli is being attended to be a user. The method 800 may be implemented by the computer device 10 described herein. At step 802, the method 800 may include presenting a plurality of periodic motion-based visual stimuli 42 having different target frequencies 44 or target codes 36, each periodic motion-based visual stimulus 42 being associated with respective interface elements of a plurality of interface elements 66. For example, the GUI 62 of an application program 64 may include a plurality of GUI elements 66 that are selectable by the user. The GUI 62 may further include a plurality of periodic motion-based visual stimuli that are associated with respective GUI elements 66.

Figure 9:
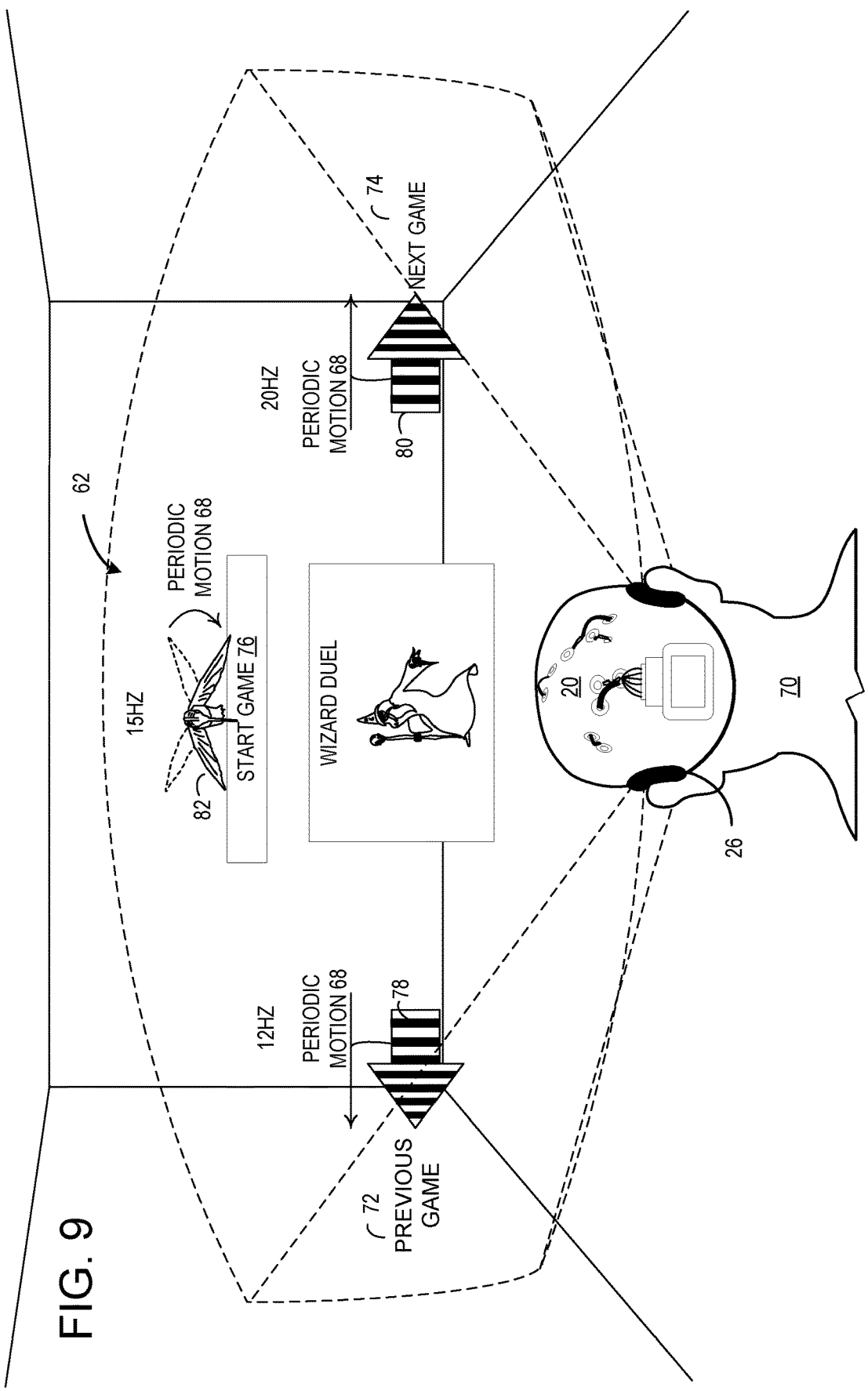
FIG. 9 shows an example GUI that implements the periodic motion-based visual stimulus that is displayed by the computer device of FIG. 1.

FIG. 9 illustrates an example GUI 62 for an application program 64 taking the form of a game library application. The GUI 62 is displayed via a display device of the HMD device 26. The user 70 is wearing the HMD device 26 and the sensor system 20. While the GUI 62 is displayed to the user 70, electrodes 22 of the sensor system 20 will captured EEG signal 24 and send that data to the HMD device 26, as described above. The HMD device 26 may then recognize user inputs to the GUI 62 using the steps of method 300. As illustrated in FIG. 9, the HMD device 26 may further be configured to present a plurality of GUI elements 66, including a previous game GUI element 72, a next game GUI element 74, and a start game GUI element 76.

The HMD device 26 may further present a plurality of periodic motion-based visual stimuli 42 having different target frequencies 44 or target codes 36. For example, the GUI 62 may include a first periodic motion-based visual stimulus 78 associated with the previous game GUI element 72, a second periodic motion-based visual stimulus 80 associated with the next game GUI element 74, and a third periodic motion-based visual stimulus 82 associated with the start game GUI element 76. Each periodic motion-based visual stimulus may be set to have a different target frequency or target code. In the illustrated example, the plurality of periodic motion-based visual stimuli are frequency-modulated, and includes a first periodic motion-based visual stimulus 78 having a target frequency of 12 Hz, the second periodic motion-based visual stimulus 80 has a target frequency of 20 Hz, and the third periodic motion-based visual stimulus 82 has a target frequency of 15 Hz.

While the user 70 is viewing the GUI 62, the EEG signal 24 data is processed by the EEG signal processing module 52, which identifies peaks in the frequency domain of the EEG signal according to the techniques described above. However, in the example illustrated in FIG. 9, all three periodic motion-based visual stimuli may be within view of the user concurrently. Thus, the frequency domain of the EEG signal 24 may potentially include three peaks, one at 12 Hz, one at 15 Hz, and one at 20 Hz in this example. Further, it should be appreciated that peaks at multiples of these frequencies may also occur for upper harmonic frequencies. It should be appreciated that the set of target frequencies including 12 Hz, 15 Hz, and 20 Hz are merely exemplary, and that the target frequencies may include other suitable values. For example, selecting target frequencies that are even periods of a frame refresh rate for the display 18 may provide the potential benefit of reducing visual flickering that may occur during presentation of the stimulus.

Figure 10:
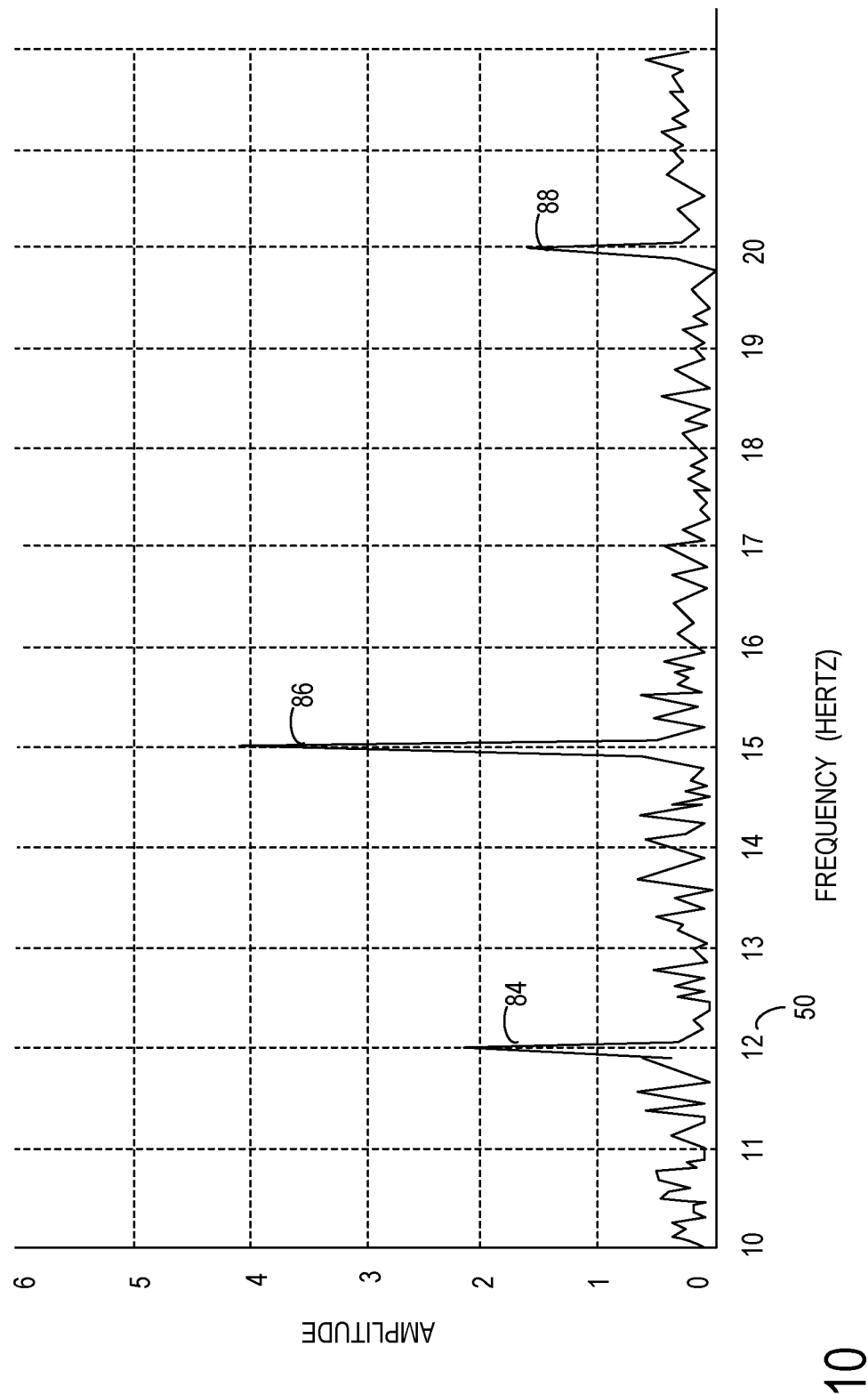
FIG. 10 shows a graph of a frequency domain of electrical activity of a user's brain captured by a sensor system of the computer device of FIG. 9.

The computer device 10 may be configured to implement method 800 to identify which periodic motion-based visual stimulus is being attended to by the user. At step 804, the method 800 may include determining that the user is attending to the periodic motion-based visual stimulus 42 based on a magnitude of the corresponding VEP feature 45 identified in the detected changes in electrical potential 46, and recognize the user input 54 based on determining that the user is attending to the periodic motion-based visual stimulus 42. FIG. 10 illustrates a graph of an example EEG signal 24 including changes in electrical potential 46 for the user 70 of FIG. 9 viewing the GUI 62. As the user sees all three periodic motion-based visual stimuli, the EEG signal 24 may include three peaks 84, 86, and 88 at frequencies that correspond to the target frequencies 44 of the three periodic motion-based visual stimuli, specifically at 12 Hz, 15 Hz, and 20 Hz in the illustrated example.

However, in this specific example, the user is focusing their attention on the third periodic motion-based visual stimulus 82, which has a target frequency of 15 Hz. Thus, as the user is attending to the third periodic motion-based visual stimulus 82, the electrical activity reflected in the user's visual cortex will have a higher magnitude in the frequency domain at the frequency that corresponds to the third periodic motion-based visual stimulus 82 compared to the other two corresponding frequencies. As shown in FIG. 10, the peak 86 for the frequency 15 Hz that corresponds to the target frequency of the third periodic motion-based visual stimulus 82 has a larger magnitude than the peaks 84 and 88 corresponding to the other periodic motion-based visual stimuli. The EEG signal processing module 52 may be configured to determine that the user is attending to the third periodic motion-based visual stimulus 82.

At step 806, the method 800 may include determining a user attended periodic motion-based visual stimulus from among the plurality of periodic motion-based visual stimuli. The computer device 10 implementing method 800 may determine the user attended periodic motion-based visual stimulus at step 804 based on the magnitudes of the identified peaks the frequency domain of the detected changes in electrical potential 46. In the example illustrated in FIGS. 9 and 10, the HMD device 26 may determine that the third periodic motion-based visual stimulus 82 is the user attended periodic motion-based visual stimulus.

At step 808, the method 800 may include recognizing the user input 54 to be directed to an interface element 66 associated with the user attended periodic motion-based visual stimulus. In the example illustrated in FIG. 9, the HMD device 26 may determine that the start game GUI element 76 is associated with the third periodic motion-based visual stimulus 82, which is the user attended stimulus in this example. The HMD device 26 may then recognize the user input 54 to be directed to the start game GUI element 76. In the illustrated example, the user input 54 may be selection of the start game GUI element 76. Accordingly, the HMD device 26 may then start the game "WIZARD DUEL" in response to the user attending to the third periodic motion-based visual stimulus 82. As discussed above, recognition of the user input 54 may be further based on other sensor data. For example, in addition to determining that the user is attending to the third periodic motion-based visual stimulus 82, the HMD device 26 may be further configured to determine that the user's gaze direction as estimated by inward facing cameras is also directed toward the start game GUI element 76 before recognizing the user input 54.

Figure 11:
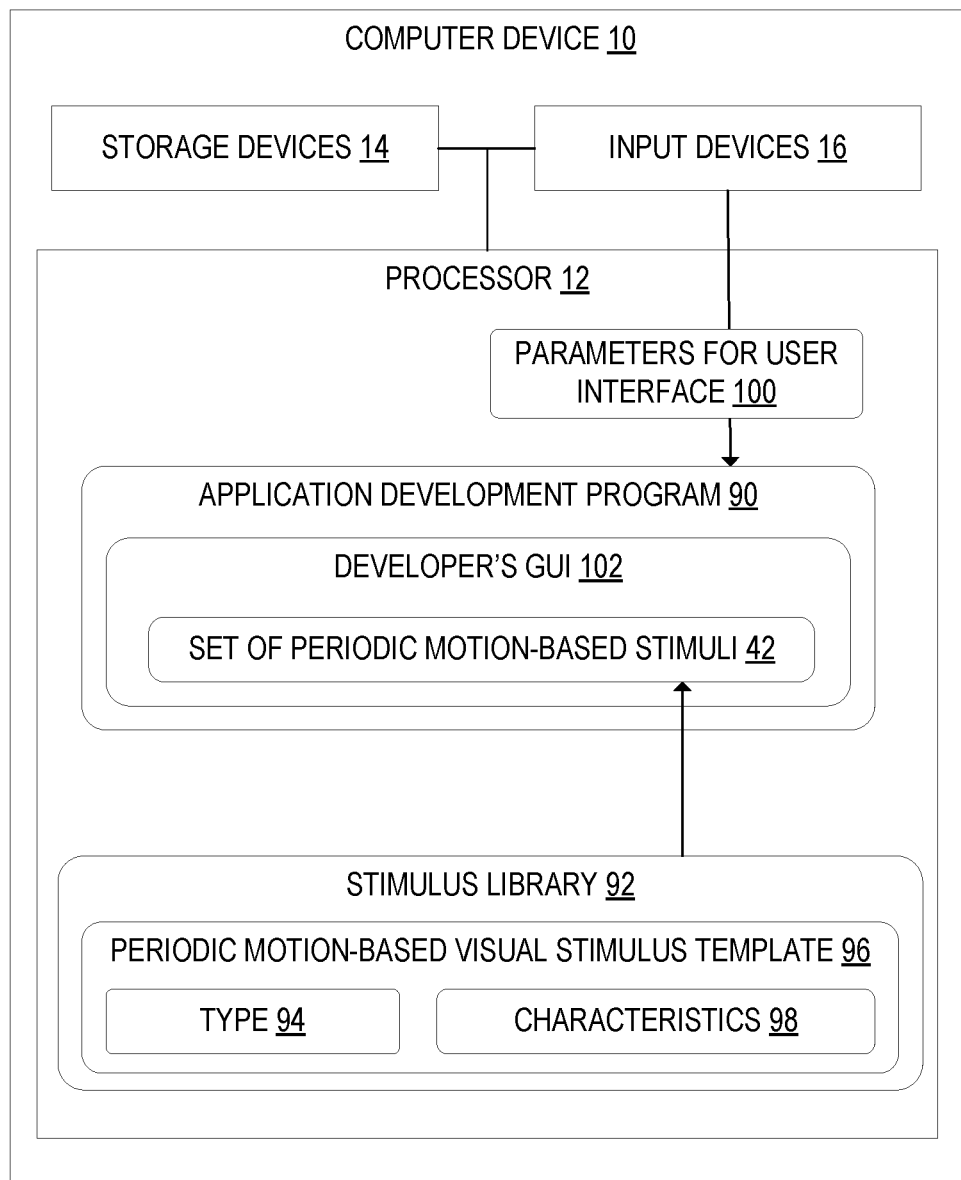
FIG. 11 shows a periodic motion-based visual stimulus development library implemented by the computer device of FIG. 1.

For developers unfamiliar with SSVEP, choosing a suitable set of periodic motion-based visual stimuli for their applications may be difficult. Thus, as illustrated in FIG. 11, the computer device 10 may be further configured to provide an application development program 90 to facilitate development of GUIs that use the periodic motion-based visual stimuli described above. The computer device 10 may store a library 92 of different types 94 of periodic motion-based visual stimuli 42. The library 92 may include templates 96 for the different types 94 of periodic motion-based visual stimuli 42. The different types 94 may, for example, include the hummingbird stimulus of FIG. 5, the windmill stimulus of FIG. 6, the changing grating pattern of FIG. 7, or any other suitable type of periodic motion-based visual stimuli 42.

The templates 96 may also include other characteristics 98 of the periodic motion-based visual stimuli 42, such as, for example, a differentiated frequency characteristic, a size characteristic, a visual contrast characteristic, and a positional separation characteristic. The differentiated frequency characteristic may include rules for how different the target frequencies 44 for a set of periodic motion-based visual stimuli of that type should be to achieve a suitable classification accuracy. For example, one particular type of periodic motion-based visual stimulus may require at least a 2 Hz difference in target frequencies to achieve a suitable classification accuracy.

The size characteristic may include rules for how small or large the periodic motion-based visual stimuli of a particular type 94 of stimuli should be to achieve a suitable classification accuracy. The positional separation characteristics may include rules for how close or far the periodic motion-based visual stimuli for a particular type 94 of stimuli should be to achieve a suitable classification accuracy. It should be appreciated that the defined characteristics 98 of the periodic motion-based visual stimuli are not limited to the examples described herein, but may include other example characteristics 98 such as, for example, color, contrast from background, etc.

The computer device 10 may be further configured to receive an input of one or more parameters 100 for a user interface via an input device 16 of the computer device 10. The parameters 100 may be sent to the application development program 90 that the user is currently developing their GUI 102. These parameters 100 may include a number of GUI elements, a position of those elements in the GUI, colors of elements, other elements included in the GUI, a size of each element, etc.

The computer device 10 may then programmatically determine a type 94 of periodic motion-based visual stimulus 42 and one or more characteristics 98 based on the received one or more parameters 100 for the user interface. The computer device 10 may determine the type 94 and the characteristics 98 based on the rules defined in the templates 96 stored in the library 92. As a specific example, a GUI that includes a large number of GUI elements may require a type 94 of periodic motion-based visual stimulus 42 that provides high classification accuracy at smaller sizes, or when placed close together. In this manner, the computer device 10 may choose types 94 and characteristics 98 for the periodic motion-based visual stimuli 42 that are suitable for the parameters 100 entered by the user. The computer device 10 may then generate a set of periodic motion-based visual stimuli 42 based on the determined type 94 and one or more characteristics 98, and provide the set to the application development program 90 for inclusion in the developer's GUI 102.

Using the techniques and processes described herein, the computer device 10 may implement periodic motion-based visual stimuli for SSVEP interfaces that reduces visual fatigue and increases the user-friendliness of SSVEP interfaces while preserving classification accuracy. The periodic motion-based visual stimuli described herein provides an improved user experienced compared to typical SSVEP interfaces that use high contrast blinking stimuli.

In some embodiments, the methods and processes described herein may be tied to a computing system of one or more computing devices. In particular, such methods and processes may be implemented as a computer-application program or service, an application-programming interface (API), a library, and/or other computer-program product.

Figure 12:
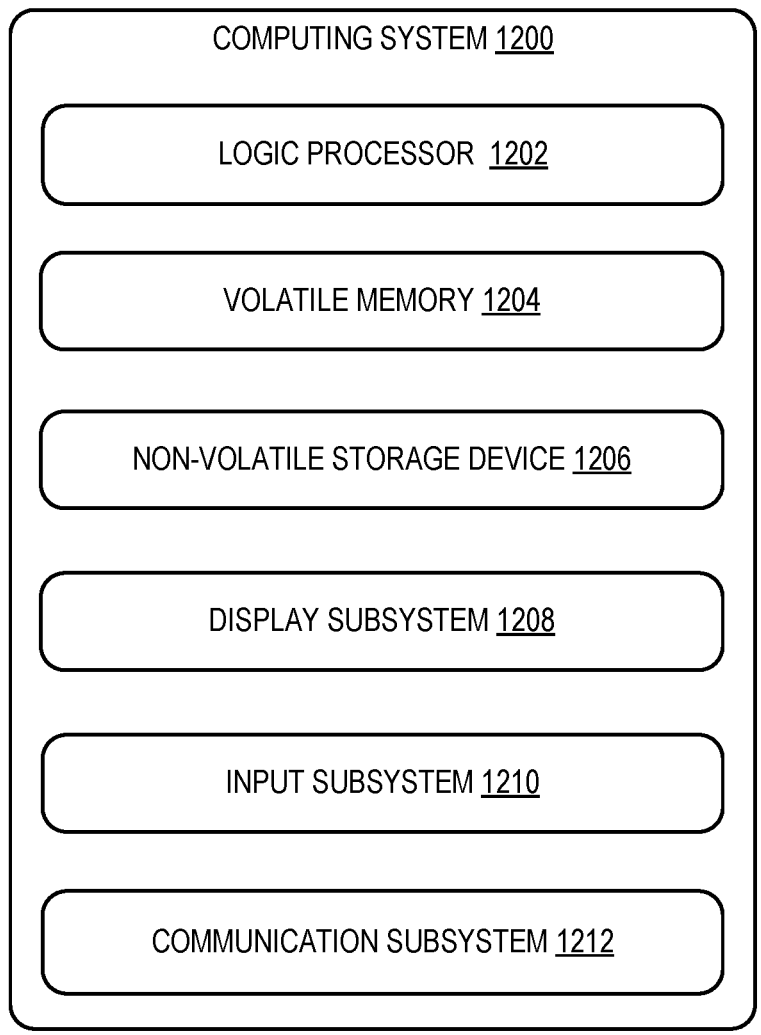
FIG. 12 shows a schematic view of an example computing environment in which the computer device of FIG. 1 may be enacted.

FIG. 12 schematically shows a non-limiting embodiment of a computing system 1200 that can enact one or more of the methods and processes described above. Computing system 1200 is shown in simplified form. Computing system 1200 may embody the computer device 10 described above and illustrated in FIG. 1. Computing system 1200 may take the form of one or more personal computers, server computers, tablet computers, home-entertainment computers, network computing devices, gaming devices, mobile computing devices, mobile communication devices (e.g., smartphone), and/or other computing devices, and wearable computing devices such as smart wristwatches and head mounted augmented reality devices.

Computing system 1200 includes a logic processor 1202 volatile memory 1204, and a non-volatile storage device 1206. Computing system 1200 may optionally include a display subsystem 1208, input subsystem 1210, communication subsystem 1212, and/or other components not shown in FIG. 12.

Logic processor 1202 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 1202 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor may be virtualized and executed by remotely accessible, networked computing devices configured in a cloud-computing configuration. In such a case, these virtualized aspects are run on different physical logic processors of various different machines, it will be understood.

Non-volatile storage device 1206 includes one or more physical devices configured to hold instructions executable by the logic processors to implement the methods and processes described herein. When such methods and processes are implemented, the state of non-volatile storage device 1206 may be transformed—e.g., to hold different data.

Non-volatile storage device 1206 may include physical devices that are removable and/or built-in. Non-volatile storage device 1206 may include optical memory (e.g., CD, DVD, HD-DVD, Blu-Ray Disc, etc.), semiconductor memory (e.g., ROM, EPROM, EEPROM, FLASH memory, etc.), and/or magnetic memory (e.g., hard-disk drive, floppy-disk drive, tape drive, MRAM, etc.), or other mass storage device technology. Non-volatile storage device 1206 may include nonvolatile, dynamic, static, read/write, read-only, sequential-access, location-addressable, file-addressable, and/or content-addressable devices. It will be appreciated that non-volatile storage device 1206 is configured to hold instructions even when power is cut to the non-volatile storage device 1206.

Volatile memory 1204 may include physical devices that include random access memory. Volatile memory 1204 is typically utilized by logic processor 1202 to temporarily store information during processing of software instructions. It will be appreciated that volatile memory 1204 typically does not continue to store instructions when power is cut to the volatile memory 1204.

Aspects of logic processor 1202, volatile memory 1204, and non-volatile storage device 1206 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 1200 typically implemented in software by a processor to perform a particular function using portions of volatile memory, which function involves transformative processing that specially configures the processor to perform the function. Thus, a module, program, or engine may be instantiated via logic processor 1202 executing instructions held by non-volatile storage device 1206, using portions of volatile memory 1204. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

When included, display subsystem 1208 may be used to present a visual representation of data held by non-volatile storage device 1206. The visual representation may take the form of a graphical user interface (GUI). As the herein described methods and processes change the data held by the non-volatile storage device, and thus transform the state of the non-volatile storage device, the state of display subsystem 1208 may likewise be transformed to visually represent changes in the underlying data. Display subsystem 1208 may include one or more display devices utilizing virtually any type of technology. Such display devices may be combined with logic processor 1202, volatile memory 1204, and/or non-volatile storage device 1206 in a shared enclosure, or such display devices may be peripheral display devices.

When included, input subsystem 1210 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity; and/or any other suitable sensor.

When included, communication subsystem 1212 may be configured to communicatively couple various computing devices described herein with each other, and with other devices. Communication subsystem 1212 may include wired and/or wireless communication devices compatible with one or more different communication protocols. As non-limiting examples, the communication subsystem may be configured for communication via a wireless telephone network, or a wired or wireless local- or wide-area network, such as a HDMI over Wi-Fi connection. In some embodiments, the communication subsystem may allow computing system 1200 to send and/or receive messages to and/or from other devices via a network such as the Internet.

The following paragraphs provide additional support for the claims of the subject application. One aspect provides a computer device comprising a display device and a sensor system configured to be mounted adjacent to a user's head and to measure an electrical potential near one or more electrodes of the sensor system. The computer device further comprises a processor configured to present a periodic motion-based visual stimulus having a changing motion that is frequency-modulated for a target frequency or code-modulated for a target code, detect changes in the electrical potential via the one or more electrodes, identify a corresponding visual evoked potential feature in the detected changes in the electrical potential that corresponds to the periodic motion-based visual stimulus, and recognize a user input to the computing device based on identifying the corresponding visual evoked potential feature. In this aspect, additionally or alternatively, the periodic motion-based visual stimulus may be code-modulated for a target code. To identify the corresponding visual evoked potential feature, the processor may be configured to identify a corresponding code in the detected changes in electrical potential that corresponds to the target code of the periodic motion-based visual stimulus. In this aspect, additionally or alternatively, the periodic motion-based visual stimulus may be frequency-modulated to change at the target frequency. To identify the corresponding visual evoked potential feature, the processor may be configured to identify a peak in a frequency domain of the detected changes in electrical potential at a corresponding frequency that corresponds to the target frequency of the periodic motion-based visual stimulus. In this aspect, additionally or alternatively, the target frequency of the periodic motion-based visual stimulus may include a fundamental frequency and one or more upper harmonic frequencies. In this aspect, additionally or alternatively, the processor may be configured to recognize the user input based on identifying peaks at corresponding frequencies that correspond to the fundamental frequency and the one or more upper harmonic frequencies of the periodic motion-based visual stimulus. In this aspect, additionally or alternatively, the periodic motion-based visual stimulus may include a periodic motion selected from the group consisting of a rotational motion, an oscillating motion, and a changing grating pattern. In this aspect, additionally or alternatively, the periodic motion-based visual stimulus may be a rapid serial visual presentation of images. In this aspect, additionally or alternatively, the display device may be a near-eye display device, and the periodic motion-based visual stimulus may be an animated three-dimensional virtual object presented by the near-eye display device. In this aspect, additionally or alternatively, to recognize the user input, the processor may be further configured to determine that the user is attending to the periodic motion-based visual stimulus based on a magnitude of the corresponding visual evoked potential feature, and recognize the user input based on determining that the user is attending to the periodic motion-based visual stimulus. In this aspect, additionally or alternatively, the processor may be further configured to present a plurality of periodic motion-based visual stimuli having different target frequencies or target codes, each periodic motion-based visual stimulus being associated with respective interface elements of a plurality of interface elements. In this aspect, additionally or alternatively, the processor may be further configured to determine a user attended periodic motion-based visual stimulus from among the plurality of periodic motion-based visual stimuli, and recognize the user input to be directed to an interface element associated with the user attended periodic motion-based visual stimulus. In this aspect, additionally or alternatively, the processor may be further configured to store a library of different types of periodic motion-based visual stimuli, receive an input of one or more parameters for a user interface, determine a type of periodic motion-based visual stimulus and one or more characteristics based on the received one or more parameters for the user interface, and generate a set of periodic motion-based visual stimuli based on the determined type and one or more characteristics. In this aspect, additionally or alternatively, the one or more characteristics may be selected from the group consisting of a differentiated frequency characteristic, a size characteristic, a visual contrast characteristic, and a positional separation characteristic.

Another aspect provides a method comprising, at a computer device having a processor and a sensor system configured to be mounted adjacent to a user's head and to measure an electrical potential near one or more electrodes of the sensor system, presenting a periodic motion-based visual stimulus having a changing motion that is frequency-modulated for a target frequency or code-modulated for a target code via a display device of the computer device. The method further comprises detecting changes in the electrical potential via the one or more electrodes, identifying a corresponding visual evoked potential feature in the detected changes in the electrical potential that corresponds to the periodic motion-based visual stimulus, and recognizing a user input to the computing device based on identifying the corresponding visual evoked potential feature. In this aspect, additionally or alternatively, the periodic motion-based visual stimulus may be code-modulated for a target code. Identifying the corresponding visual evoked potential feature may further comprise identifying a corresponding code in the detected changes in electrical potential that corresponds to the target code of the periodic motion-based visual stimulus. In this aspect, additionally or alternatively, the periodic motion-based visual stimulus may be frequency-modulated to change at the target frequency. Identifying the corresponding visual evoked potential feature may further comprise identifying a peak in a frequency domain of the detected changes in electrical potential at a corresponding frequency that corresponds to the target frequency of the periodic motion-based visual stimulus. In this aspect, additionally or alternatively, recognizing the user input may further comprise determining that the user is attending to the periodic motion-based visual stimulus based on a magnitude of the corresponding visual evoked potential feature, and recognizing the user input based on determining that the user is attending to the periodic motion-based visual stimulus. In this aspect, additionally or alternatively, the method may further comprise presenting a plurality of periodic motion-based visual stimuli having different target frequencies or target codes, each periodic motion-based visual stimulus being associated with respective interface elements of a plurality of interface elements. In this aspect, additionally or alternatively, the method may further comprise determining a user attended periodic motion-based visual stimulus from among the plurality of periodic motion-based visual stimuli, and recognizing the user input to be directed to an interface element associated with the user attended periodic motion-based visual stimulus.

Another aspect provides a computer device comprising a display device, and a sensor system configured to be mounted adjacent a user's head and to measure an electrical potential near one or more electrodes of the sensor system. The computer device further comprises a processor configured to present a plurality of interface elements via the display device, and present a plurality of periodic motion-based visual stimuli. Each periodic motion-based visual stimulus is associated with respective interface elements of the plurality of interface elements. The processor is further configured to detect changes in the electrical potential via the one or more electrodes, and determine that the user is attending to a user attended periodic motion-based visual stimulus from among the plurality of periodic motion-based visual stimuli based on identifying a corresponding visual evoked potential feature in the detected changes in the electrical potential that corresponds to the user attended periodic motion-based visual stimulus. The processor is further configured to recognize a user input directed at an interface element that is associated with the user attended periodic motion-based visual stimulus.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A computer device comprising:
   a display device;
   a sensor system configured to be mounted adjacent to a user's head and to measure an electrical potential near one or more electrodes of the sensor system; and
   a processor configured to:
      present a periodic motion-based visual stimulus having a changing motion that is frequency-modulated for a target frequency, wherein:
         the periodic motion-based visual stimulus is frequency-modulated to change at the target frequency; and
         the target frequency of the periodic motion-based visual stimulus includes a fundamental frequency and one or more harmonic frequencies;
      detect changes in the electrical potential via the one or more electrodes;
      identify a corresponding visual evoked potential feature in the detected changes in the electrical potential that corresponds to the periodic motion-based visual stimulus, wherein to identify the corresponding visual evoked potential feature, the processor is configured to identify a peak in a frequency domain of the detected changes in electrical potential at a corresponding frequency that corresponds to the target frequency of the periodic motion-based visual stimulus;
      determine that the user is attending to the periodic motion-based visual stimulus based on a magnitude of the corresponding visual evoked potential feature; and
      recognize a user input to the computer device based on determining that the user is attending to the periodic motion-based visual stimulus.

2. The computer device of claim 1, wherein the processor is configured to recognize the user input based on identifying peaks at corresponding frequencies that correspond to the fundamental frequency and the one or more upper harmonic frequencies of the periodic motion-based visual stimulus.

3. The computer device of claim 1, wherein the periodic motion-based visual stimulus includes a periodic motion selected from the group consisting of a rotational motion, an oscillating motion, and a changing grating pattern.

4. The computer device of claim 1, wherein the periodic motion-based visual stimulus is a rapid serial visual presentation of images.

5. The computer device of claim 1, wherein the display device is a near-eye display device, and wherein the periodic motion-based visual stimulus is an animated three-dimensional virtual object presented by the near-eye display device.

6. The computer device of claim 1, wherein the magnitude is a magnitude in the frequency domain of the electrical potential.

7. The computer device of claim 1, wherein the processor is further configured to present a plurality of periodic motion-based visual stimuli having different target frequencies, each periodic motion-based visual stimulus being associated with respective interface elements of a plurality of interface elements.

8. The computer device of claim 7, wherein the processor is further configured to:
determine a user attended periodic motion-based visual stimulus from among the plurality of periodic motion-based visual stimuli; and
recognize the user input to be directed to an interface element associated with the user attended periodic motion-based visual stimulus.

9. The computer device of claim 8, wherein the processor is further configured to select, as the user attended periodic motion-based visual stimulus, a periodic motion-based visual stimulus of the plurality of periodic motion-based visual stimuli that has a highest-magnitude visual evoked potential feature among the respective visual evoked potential features of the periodic motion-based visual stimuli.

10. The computer device of claim 1, wherein the computer device is a head-mounted display device.

11. A method comprising:
at a computer device having a processor and a sensor system configured to be mounted adjacent to a user's head and to measure an electrical potential near one or more electrodes of the sensor system:
presenting a periodic motion-based visual stimulus having a changing motion that is frequency-modulated for a target frequency, wherein:
the periodic motion-based visual stimulus is frequency-modulated to change at the target frequency; and
the target frequency of the periodic motion-based visual stimulus includes a fundamental frequency and one or more harmonic frequencies;
detecting changes in the electrical potential via the one or more electrodes;
identifying a corresponding visual evoked potential feature in the detected changes in the electrical potential that corresponds to the periodic motion-based visual stimulus, wherein identifying the corresponding visual evoked potential feature includes identifying a peak in a frequency domain of the detected changes in electrical potential at a corresponding frequency that corresponds to the target frequency of the periodic motion-based visual stimulus;
determining that the user is attending to the periodic motion-based visual stimulus based on a magnitude of the corresponding visual evoked potential feature; and
recognizing a user input to the computer device based on determining that the user is attending to the periodic motion-based visual stimulus.

12. The method of claim 11, further comprising presenting a plurality of periodic motion-based visual stimuli having different target frequencies, each periodic motion-based visual stimulus being associated with respective interface elements of a plurality of interface elements.

13. The method of claim 12, further comprising:
determining a user attended periodic motion-based visual stimulus from among the plurality of periodic motion-based visual stimuli; and
recognizing the user input to be directed to an interface element associated with the user attended periodic motion-based visual stimulus.

14. The method of claim 12, wherein determining the user attended periodic motion-based visual stimulus includes selecting, as the user attended periodic motion-based visual stimulus, a periodic motion-based visual stimulus of the plurality of periodic motion-based visual stimuli that has a highest-magnitude visual evoked potential feature among the respective visual evoked potential features of the periodic motion-based visual stimuli.

15. A computer device comprising:
a display device;
a sensor system configured to be mounted adjacent a user's head and to measure an electrical potential near one or more electrodes of the sensor system; and
a processor configured to:
present a plurality of interface elements via the display device;
present a plurality of periodic motion-based visual stimuli, each periodic motion-based visual stimulus being associated with respective interface elements of the plurality of interface elements, wherein:
the periodic motion-based visual stimuli are frequency-modulated to change at respective target frequencies; and
the target frequency of each of the periodic motion-based visual stimuli includes a fundamental frequency and one or more harmonic frequencies;
detect changes in the electrical potential via the one or more electrodes;
determine that the user is attending to a user attended periodic motion-based visual stimulus from among the plurality of periodic motion-based visual stimuli at least in part by:
identifying a plurality of visual evoked potential features that correspond to the plurality of periodic motion-based visual stimuli in the detected changes in the electrical potential, wherein to identify each of the visual evoked potential features, the processor is configured to identify a respective peak in a frequency domain of the detected changes in electrical potential at a corresponding frequency that corresponds to the target frequency of the periodic motion-based visual stimulus;
determining respective magnitudes of the plurality of visual evoked potential features; and selecting, as the user attended periodic motion-based visual stimulus, a periodic motion-based visual stimulus of the plurality of periodic motion-based visual stimuli that has a highest-magnitude visual evoked potential feature among the respective visual evoked potential features of the periodic motion-based visual stimuli; and recognize a user input directed at an interface element that is associated with the user attended periodic motion-based visual stimulus.

\* \* \* \* \*